(12) United States Patent
Jones

(10) Patent No.: US 8,362,036 B2
(45) Date of Patent: Jan. 29, 2013

(54) COMPOSITION AND METHOD OF TREATING A SORE THROAT

(76) Inventor: Thomas L. Jones, Asheville, NC (US)

( * ) Notice: Subject to any disclaimer, the term of this patent is extended or adjusted under 35 U.S.C. 154(b) by 34 days.

(21) Appl. No.: 12/776,526

(22) Filed: May 10, 2010

(65) Prior Publication Data

US 2010/0221342 A1    Sep. 2, 2010

Related U.S. Application Data

(63) Continuation of application No. 11/456,890, filed on Jul. 12, 2006, now Pat. No. 7,754,234.

(51) Int. Cl.
*A61K 31/445* (2006.01)
*A61K 31/21* (2006.01)

(52) U.S. Cl. ........................ 514/315; 514/506

(58) Field of Classification Search .................. 514/315, 514/506
See application file for complete search history.

(56) References Cited

U.S. PATENT DOCUMENTS

| | | | |
|---|---|---|---|
| 4,163,777 A | 8/1979 | Mitra | |
| 4,396,604 A | 8/1983 | Mitra | |
| 4,442,113 A * | 4/1984 | Lassen et al. | 514/317 |
| 4,594,259 A * | 6/1986 | Baker et al. | 426/613 |
| 5,102,666 A | 4/1992 | Acharya | |
| 5,409,709 A * | 4/1995 | Ozawa et al. | 424/464 |
| 5,686,094 A | 11/1997 | Acharya | |
| 5,889,057 A * | 3/1999 | Barrett et al. | 514/570 |
| 6,183,775 B1 | 2/2001 | Ventouras et al. | |
| 7,754,234 B2 * | 7/2010 | Jones | 424/441 |
| 2003/0181383 A1 | 9/2003 | Podolsky | |
| 2004/0105823 A1 * | 6/2004 | Kamasaka et al. | 424/49 |
| 2004/0224076 A1 * | 11/2004 | Derrien et al. | 426/648 |

FOREIGN PATENT DOCUMENTS

WO    WO 03089007    * 10/2003

OTHER PUBLICATIONS

The PDR Pocket Guide to Prescription Drugs, 7th Edition, 2005, pp. 1690, 1703 and 1712-1713.
Facts and Comparisons, 1993 Edition, pp. 2392-2393.
"Lidocaine", http://www.drugs.com/pro/lidocaine.html, 2008.
"Anesthetics (Topical)", http://www.drugs.com/cons/anesthetics-topical.html, 2008.

* cited by examiner

*Primary Examiner* — Alton Pryor
(74) *Attorney, Agent, or Firm* — Connolly Bove Lodge & Hutz LLP

(57) ABSTRACT

A composition comprising an antacid, and a local, topical anesthetic. The composition is used to relieve pain or discomfort associated with a sore throat, and therefore, the invention is also directed to a method of alleviating the pain or discomfort associated with a sore throat comprising instructing a human to orally administer the composition.

20 Claims, No Drawings

COMPOSITION AND METHOD OF TREATING A SORE THROAT

CROSS REFERENCE TO RELATED APPLICATIONS

This application is a Continuation of co-pending application Ser. No. 11/456,890, filed on Jul. 12, 2006, and for which priority is claimed under 35 U.S.C. §120. The entire contents of these applications are hereby incorporated by reference.

FIELD OF THE INVENTION

The invention relates to a composition comprising an antacid and a local, topical anesthetic. As the composition dissolves or disintegrates in the mouth the antacid and local, topical anesthetic is released from the composition thereby relieving the discomfort often associated with a sore throat.

BACKGROUND OF THE INVENTION

The delivery of drugs through the buccal mucosa is a very well known and convenient way of administering a number of active ingredients for either local or systemic action. Chewable tablets, lozenges and other similar oral dosage forms have been present on the market for many years. These galenical forms often consist of a soluble diluent, such as sugar, lactose, mannitol or sorbitol, and a binder. Lubricants, flavors, sweetening agents, or taste correctors are also often present in these dosage forms. These forms dissolve relatively rapidly once in the mouth, within either a few seconds or up to 10 minutes, and deliver both soluble and insoluble active ingredients to the buccal cavity.

SUMMARY OF THE INVENTION

The invention is directed to a composition comprising an antacid, and a local, topical anesthetic. The composition is used to relieve pain or discomfort associated with a sore throat, and therefore, the invention is also directed to a method of alleviating the pain or discomfort associated with a sore throat comprising instructing a human to orally administer a composition comprising an antacid and a local, topical anesthetic.

DETAILED DESCRIPTION OF THE INVENTION

A sore throat can develop for a number of reasons including a viral or bacterial infection, or a common or seasonal allergy. Often associated with an infection, common or seasonal allergy is some degree of nasal or sinus congestion. This congestion is typically referred to as post-nasal drip, in which mucous originating on the surface of the nasal mucosa or the sinus mucosa drains onto the upper esophagus. The accumulation of nasal mucosa in the upper esophagus also stimulates the swallowing reflex often associated with a sore throat. The swallowing reflex transports the acidic mucous into relatively constant contact with the region of the throat. The acidic nature of the mucous from the sinus mucosa or nasal mucosa erodes the epithelial tissue of the throat thereby exposing the underlying tissue to the acidic mucous. The nerve endings in the underlying tissue in contact with the acidic mucosa cause what we identify as the discomfort or pain associated with a sore throat. The more inflamed the nasal mucosa or the sinus mucosa, the greater the production of the acidic mucous, the greater the erosion and the greater the severity of the pain and discomfort associated with the sore throat.

The composition comprises an antacid to neutralize in-part the acidic nature of the mucous, which in turn, helps to minimize the amount of erosion and/or subsequent exposure of the underlying tissue and exposed nerve endings to an acidic environment. The relatively slow release of the antacid from the composition helps to counteract the acidic mucosa from the sinus that is constantly draining into the upper esophagus and being swallowed. The composition provides a controlled antacid delivery form for the administration of an antacid. As the controlled dosage form, e.g., a lozenge, slowly dissolves in the mouth, a sustained release of the antacid is achieved which neutralizes the acidic environment in the throat region caused by the acidic mucosa. Surprisingly, only a small amount of antacid is needed to adjust the pH of the throat region and provide relief for tissues inflamed by the acidic mucosa.

The antacid can be one or more of antacid agents such as sodium, calcium, magnesium or aluminum salts that are commonly used to neutralize gastric fluids. Exemplary antacids are sodium bicarbonate, sodium citrate, calcium carbonate, calcium phosphate, magnesium oxide, magnesium hydroxide, magnesium carbonate, magnesium trisilicate, aluminum carbonate and aluminum hydroxide. Other suitable antacids include dihydroxy aluminum sodium carbonate, dihydroxy aluminum aminoacetate and magnesium hydroxy aluminates. Various other co-precipitates of aluminum hydroxides or carbonates with magnesium hydroxides or carbonates, hexitols, aminoacetic acid or the like can also be used.

The process of neutralizing the acid mucous brings relief to the discomfort associated with a sore throat. In many embodiments, the antacid composition includes a combination of magnesium and aluminum salts, calcium and aluminum salts or magnesium and calcium salts. The antacid is provided in a sufficient quantity to effect the acid neutralization of the throat region over a selected period, for example, 15 to 60 minutes. To that end each lozenge has from 10 to 40 meq. of antacid, preferably from 20 to 30 meq of antacid.

The composition also contains one or more local, topical anesthetic agents. The local, topical anesthetic agents also help to alleviate the pain or discomfort often associated with a sore throat, particularly as the throat undergoes a swallowing-type action. Exemplary local, topical anesthetic agents include lidocaine, benzocaine, tetracaine, dyclonine and mixtures thereof. Benzocaine and tetracaine are two of the preferred local, topical anesthetic agents used in the composition.

The composition can also contain one or more sweeteners to make it more palatable. For example, any sugar or sugar-free sweetener, e.g. maltitol, xylitol, sorbitol, mannitol, lactose, dextrose, saccharose or fructose, or any mixture thereof, e.g. a mixture of xylitol and sorbitol, such as Xylisorb® can be used in the composition. Some of the more preferred sweeteners include maltitol, xylitol, mannitol, dextrose, sorbitol, fructose, or any mixture thereof. The sweeteners can be present in an amount of from 30 to 95 wt. %, from 50 to 90 wt. % and from 70 to 90 wt. % of the total composition.

The composition is formulated as a dosage form that slowly dissolves or disintegrates in the mouth. As a result, the composition will typically contain a relative large amount of a sweetener. Suitable good tasting sweeteners include the sugar alcohols mannitol, sorbitol and xylitol. Sugar alcohols are preferred because they provide compositions such as a lozenge or a chewing gum that is "sugarless". Mannitol is one of the preferred sugar alcohols because it is less soluble than sorbitol. Also, mannitol provides a slightly sweet product with a particularly refreshing or cooling affect.

If the composition includes a sugar alcohol, it may be necessary to add an artificial sweetener to provide a composition with an acceptable taste. Although mannitol is a preferred sweetener, it may be substituted by or used in combination with other sugar alcohols. If a candy like lozenge is desired, sucrose, dextrose or the like can be used in place of the sugar alcohol. Because these sugars are more soluble than mannitol, the amount of the swelling agent or matrix forming agents should be increased to provide a composition in a dosage form that will release the antacid and local, topical anesthetic over a selected time period, e.g., 10 to 30 minutes.

One or more matrix-forming agents that are capable of forming a matrix that can be present in the composition include, for example, polyacrylates, which means homo- or co-polymers of alkyl esters, especially methyl and ethyl esters but also e.g. substituted alkyl esters such as dimethylaminoethyl esters, of acrylic acid and/or methacrylic acid, e.g. Eudragit® products such as Eudragite® S, Eudragit® NE, Eudragit® E or Eudragit® L of Rochm Pharma GmbH, Darmstadt (Germany). Other matrix-forming agents include e.g. ethyl cellulose, e.g. Aquacoat® products such as Aquacoat® ECD 30 of FMC Corp., Philadelphia (USA); polyvinylchloride, cellulose acetate, cellulose acetate phthalate or shellac. Again, mixtures of more than one of the matrix-forming agent can also be present in the composition. The matrix-forming agent is typically present in an amount of from 0.5 to 30 wt. %, from 0.5 to 24 wt. % and from 3 to 10 wt. %, based on the total composition.

Some of the more preferred matrix-forming agents include polyacrylates, and especially such polyacrylates which are in the form of an aqueous dispersion, for example Eudragit® NE 30D.

In the manufacture of the composition, the matrix-forming agent can be applied as an aqueous dispersion (pseudolatex), as a non-aqueous dispersion (using an organic solvent) or in solid form. The matrix-forming agents are intimately mixed with the other components of the composition.

The composition can also contain one or more swellable polymers selected from a naturally occurring or synthetically obtained swellable polymer that is pharmaceutically acceptable. Examples of some useful swellable polymers include xanthan gum, guar gum, alginic acid or a salt thereof, such as sodium alginate, pectins, polyvinyl alcohol, polysaccharides and swellable cellulose derivatives such as sodium or calcium carboxymethylcellulose. Again, a mixture of more than one of the swellable polymers can be present in the composition. The one or more swellable polymers can be present in an amount of from 0.5 to 30 wt. %, from 0.5 to 24 wt. % and from 3 up to 10 wt. %, of the total composition.

Some of the more preferred swellable polymers include xanthan gum, guar gum, alginic acid or a salt thereof, such as sodium alginate, and swellable cellulose derivatives such as sodium or calcium carboxymethylcellulose, hydroxypropylmethylcellulose, hydroxyethylcellulose or hydroxypropylcellulose. One of the more preferred swellable polymers is xanthan gum.

A water insoluble lipid material can also be present in the composition as a swelling agent. This lipid material can be a hydrophobic metal salt of a fatty acid such as stearic acid, palmetic acid, oleic acid and lauric acid. Applicable metals for formation of the above salts include magnesium, calcium and aluminum. Of these materials, magnesium and calcium stearate are preferred.

As the composition dissolves or disintegrates in the mouth, e.g., by the sucking of a lozenge, the swellable polymers swell on the surface of the lozenge. Small pieces of the swellable polymer erode from the surface of the lozenge together with the matrix-forming agent. The rate at which the lozenge dissolves in the mouth will depend on the formulation. A more slowly dissolving lozenge is obtained, if the amount of the matrix-forming agent, e.g. a polyacrylate dispersion, and/or the amount of the swellable polymer, e.g. xanthane gum, is increased.

The composition can also contain an anti-inflammatory agent. One particular anti-inflammatory agent present in the composition is flurbiprofen [2-(2-fluoro-4-biphenylyl)propionic] acid, which is a non-steroidal anti-inflammatory agent with known analgesic activity. The flurbiprofen molecule-exists in two enantiomeric forms and the term flurbiprofen as used herein includes the individual enantiomers and mixtures thereof in any proportion including a 1:1 mixture which is herein referred to as racemic flurbiprofen. Flurbiprofen can exist in the form of pharmaceutically acceptable salts or in the form of derivatives such as esters and such salts or esters are embraced by the term "flurbiprofen" as used herein.

The flurbiprofen is present in the composition in an amount from 2.5 to 20 mg preferably 5 to 12.5 mg. Where a pharmaceutically acceptable salt of flurbiprofen is used, the amount of the salt used should be such as to provide the desired amount of flurbiprofen. Suitable salts include the alkali metal salts eg the sodium salt or amino acid salts eg the lysine, arginine or meglumine salts of flurbiprofen.

The compositions can also contain one or more auxiliary agents known in the art and include lubricants, flavors, aromas, colorants, diluents, preservatives, glidants, e.g. colloidal silicium dioxide, and the like.

The composition can be provided as a lozenge, which can be prepared by several known methods including:

(1) a traditional wet granulation process incorporating all ingredients, and subsequent compression, or (2) a two stage process consisting of a granulation stage of only some of the ingredients, which is followed by the addition of the other ingredients, e.g. the active substance, in the external phase (see Examples 1, 2, 3 and 5), and subsequent compression, or (3) a direct compression process without a granulation stage (see Example 4).

EXAMPLE 1

Composition (for 1000 Lozenges)

Benzocaine 20.0 g; Maltitol 880.0 g; Sodium bicarbonate 20.0 g; Polyacrylate dispersion 30% 50.0 g (dry mass); Xanthane gum 40.0 g; Colloidal anhydrous silica 15.0 g; and Magnesium stearate 20.0 g.

To a fluid bed mix containing the maltitol, sodium carbonate and ⅔ of the colloidal anhydrous silica is added the polyacrylate dispersion using a contra-current fluid bed granulation. The addition of the benzocaine, xanthane gum, the remaining ⅓ of the colloidal anhydrous silica and the magnesium stearate follows. The mixture is compressed to produce 15 mm biconvex round lozenges with a mass of about 1045 mg each.

EXAMPLE 2

Composition (for 1000 Lozenges)

Benzocaine 50.0 g; Maltitol 880.0 g; Sodium carbonate anhydrous 40.0 g; Polyacrylate dispersion 30% 70.0 g (dry mass); Xanthane gum 60.0 g; Colloidal anhydrous silica 15.0 g; Peppermint 30.0 g; Levomenthol 3.0 g; Saccharine sodium 5.0 g; and Magnesium stearate 20.0 g.

To a fluid bed mix containing the maltitol, sodium carbonate anhydrous, and ⅔ of the colloidal anhydrous silica is added the polyacrylate dispersion using a contra-current fluid bed granulation. The addition of the benzocaine, xanthane gum, the remaining ⅓ of the colloidal anhydrous silica, the levomenthol, peppermint, saccharine sodium and the magnesium stearate follows. The mixture is compressed to produce 15 mm biconvex round lozenges with a mass of about 1173 mg each.

EXAMPLE 3

Composition (for 1000 Lozenges)

Benzocaine 50.0 g; Xylitol 880.0 g; Sodium carbonate anhydrous 40.0 g; Polyacrylate dispersion 30% 50.0 g (dry mass); Xanthane gum 40.0 g; Colloidal anhydrous silica 15.0 g; Cinnamon flavour 15.0 g; Saccharine sodium 5.0 g; and Magnesium stearate 20.0 g.

To a fluid bed mix containing the maltitol, sodium carbonate anhydrous, and ⅔ of the colloidal anhydrous silica is added the polyacrylate dispersion using a contra-current fluid bed granulation. The addition of the benzocaine, xanthane gum, the remaining ⅓ of colloidal anhydrous silica, the levomenthol, peppermint, saccharine sodium and the magnesium stearate follows. The mixture is compressed to produce 15 mm biconvex round lozenges with a mass of about 1115 mg each.

EXAMPLE 4

Composition (for 1000 Lozenges)

Benzocaine 50.0 g; Xylisorb® (a mixture of xylitol and sorbitol) 850.0 g; Sodium carbonate anhydrous 40.0 g; Eudragit® S-100 100.0 g; Xanthane gum 40.0 g; Colloidal anhydrous silica 5.0 g; Peppermint 30.0 g; Levomenthol 3.0 g; Saccharine sodium 5.0 g; and Magnesium stearate 20.0 g.

Mix all the ingredients together, except for the magnesium stearate, and screen through a Frewitt fitted with a screen of 0.63 mm aperture size. Add the magnesium stearate and mix for 5 minutes. The mixture is compressed to produce 15 mm biconvex round lozenges with a mass of about 11143 mg each.

EXAMPLE 5

Composition (for 1000 Lozenges)

Benzocaine 50.0 g; Maltitol 880.0 g; Sodium carbonate 10.0 g; Sodium bicarbonate 20.0 g; Polyacrylate dispersion 30% 50.0 g (dry mass); Xanthane gum 40.0 g; Colloidal anhydrous silica 15.0 g; Levomenthol 3.0 g; Peppermint oil 5.0 g; Aspartame 10.0 g; and Magnesium stearate 20.0 g To a fluid bed mix containing the maltitol, sodium carbonate, sodium bicarbonate and ⅔ of the colloidal anhydrous silica is added the polyacrylate dispersion using a contra-current fluid bed granulation. The addition of the benzocaine, xanthane gum, the remaining ⅓ of the colloidal anhydrous silica, the magnesium stearate, levomenthol, peppermint oil, and aspartame follows. The mixture is compressed to produce 15 mm biconvex round lozenges with a mass of about 1103 mg.

EXAMPLES 6

A wet granulation having the composition shown in Table 1 is prepared as follows: The mannitol, aluminum hydroxide-magnesium carbonate coprecipitate and magnesium carbonate are mixed in a twin shell blender for 5 minutes. The gelatin is dissolved in water and heated to 60° C. The gelatin solution is mixed with the above-described blend in a Simpson mixmuller to form a wet granulation. The wet granulation is spread on a tray and dried at 60° C. for 8 hours. The dried granulation is then passed through a Erweka granulator to reduce the dried material to an 18 mesh or finer particle size. This dried material is called the raw granulation.

TABLE 1

| | |
|---|---|
| Mannitol Powder | 48.17 wt. % |
| Aluminum Hydroxide-Magnesium Carbonate Coprecipitate | 25.74 wt. % |
| Magnesium Carbonate | 16.79 wt. % |
| Benzocaine | 5.0 wt. % |
| Gelatin Solution, 10% weight/weight | 4.33 wt. %. |

Lozenges having the composition shown in Table 2 are prepared as follows. The raw granulation, sodium carboxymethyl cellulose, calcium stearate, talc and flavorant are mixed for 15 minutes in a twin shell blender. This mixture is then made into lozenges on a Stokes RD3 tablet press with ⅝ in. die and deep concave punches at a pressure of 7 tons. The lozenges will have 18 meq. of antacid neutralizing capacity.

TABLE 2

| | |
|---|---|
| Raw Granulation | 91.33 wt. % |
| Sodium Carboxymethyl Cellulose | 5.00 wt. % |
| Calcium Stearate | 1.00 wt. % |
| Talc | 1.00 wt. % |
| Flavorant | 1.67 wt. % |
| Benzocaine | 5.0 wt. % |

EXAMPLE 7

A raw granulation having the composition shown in Table 3 is prepared according to the procedure of Example 6 except that calcium carbonate is used as the antacid component and starch paste is used as the auxiliary binder. The wet granulation is dried at 60° C. for 24 hours. Lozenges having the composition are prepared following the procedure of Example 6 with the exception that the raw granulation mix of Table 3 is used.

TABLE 3

| | |
|---|---|
| Mannitol Powder | 19.63% |
| Calcium Carbonate | 71.75 wt. % |
| Benzocaine | 5.0 wt. % |
| Starch Paste, 10% weight/weight | 3.92% |

EXAMPLE 8

A raw granulation having the composition shown in Table 4 is prepared according to the procedure of Example 6.

TABLE 4

| | |
|---|---|
| Mannitol Powder | 53.87 wt. % |
| Aluminum Hydroxide-Magnesium Carbonate Coprecipitate | 9.43 wt. % |
| Magnesium Carbonate | 13.47 wt. % |
| Calcium Carbonate | 11.52 wt. % |
| Benzocaine | 2.0 wt. % |
| Starch Paste, 10% weight/weight | 4.71 wt. % |

Lozenges having the composition shown in Table 5 were prepared following the procedure of Example 6. The lozenges are hard, slow dissolving and will have 24 meq. of antacid neutralizing capacity.

TABLE 5

| Raw Granulation | 93.34 wt. % |
|---|---|
| Sodium Carboxymethyl Cellulose | 3.00 wt. % |
| Calcium Stearate | 1.00 wt. % |
| Talc | 1.00 wt. % |
| Flavorant | 1.66 wt. % |
| Benzocaine | 2.0 wt. % |

EXAMPLE 9

A raw granulation having the composition shown in Table 6 is prepared according to the procedure of Example 6.

TABLE 6

| Mannitol Powder | 31.53 wt. % |
|---|---|
| Sorbitol Solution, 10% weight/weight | 4.74 wt. % |
| Aluminum Hydroxide-Magnesium Carbonate Coprecipitate | 14.34 wt. % |
| Magnesium Hydroxide | 40.37 wt. % |
| Benzocaine | 2.0 wt. % |
| Gelatin Solution, 15% weight/weight | 7.12 wt. % |

Lozenges having the composition shown in Table 7 are prepared following the procedure of Example 6. The lozenges will have 33 meq. of acid neutralizing capacity.

TABLE 7

| Raw Granulation | 88.34 wt. % |
|---|---|
| Sodium Carboxymethyl Cellulose | 5.00 wt. % |
| Calcium Stearate | 2.00 wt. % |
| Talc | 1.00 wt. % |
| Flavorant | 1.66 wt. % |
| Benzocaine | 2.0 wt. % |

EXAMPLE 10

A raw granulation having the composition shown in Table 8 is prepared according to the procedure of Example 9.

TABLE 8

| Mannitol Powder | 47.88 wt. % |
|---|---|
| Sorbitol Solution, 10% weight/weight | 4.40 wt. % |
| Aluminum Hydroxide-Magnesium Carbonate Coprecipitate | 13.57 wt. % |
| Magnesium Carbonate | 25.53 wt. % |
| Benzocaine | 2.0 wt. % |
| Gelatin Solution, 15% weight/weight | 6.60 wt. % |

Lozenges having the composition shown in Table 9 are prepared following the procedure of Example 6 except that xanthan gum is substituted for the sodium carboxymethyl cellulose.

TABLE 9

| Raw Granulation | 91.59 wt. % |
|---|---|
| Xanthan Gum | 3.00 wt. % |
| Calcium Stearate | 1.00 wt. % |
| Talc | 1.00 wt. % |
| Flavorant | 1.41 wt. % |
| Benzocaine | 2.0 wt. % |

I claim:

1. A composition consisting essentially of an antacid, selected from the group consisting of sodium, calcium, magnesium, aluminum salts, and combinations thereof, wherein the antacid provides from 10 to 40 meq. of antacid neutralizing capacity; a local, topical anesthetic selected from the group consisting of lidocaine, benzocaine, tetracaine, dyclonine, and combinations thereof; sweetener; 0.5 to 30% by weight of one or more matrix-forming agents, 0.5 to 30% by weight of one or more swellable polymers; and a swelling agent, to thereby provide a sustained release of said antacid, and slow dissolution or disintegration of said composition in the mouth of a subject.

2. The composition according to claim 1, wherein the antacid is selected from the group consisting of magnesium carbonate, calcium carbonate, magnesium hydroxide, aluminum hydroxide, and combinations thereof.

3. The composition according to claim 1 further comprising an anti-inflammatory agent.

4. The composition according to claim 3, wherein the anti-inflammatory agent is flurbiprofen.

5. The composition according to claim 1 further comprising an auxiliary agent.

6. The composition according to claim 5 wherein the auxiliary agent is selected from the group consisting of a lubricant, coloring agent, a flavoring agent, aroma, diluent, preservative, glidant, and combinations thereof.

7. The composition according to claim 1, wherein the one or more swellable polymers is selected from the group consisting of pectin, xanthum gum, and cellulose derivatives.

8. The composition according to claim 1, wherein the sweetener is selected from the group consisting of maltitol, xylitol, sorbitol, mannitol, lactose, dextrose, saccharose, fructose, and combinations thereof.

9. The composition according to claim 1, wherein the local, topical anesthetic is benzocaine.

10. The composition according to claim 1, wherein the local, topical anesthetic is present from 0.5 wt. % to 20 wt. %.

11. A lozenge comprising the composition according to claim 1.

12. A chewing gum comprising the composition according to claim 1.

13. A sort throat composition according to claim 1.

14. The composition according to claim 1, wherein the local, topical anesthetic is present from 0.5 wt. % to 20 wt. %.

15. The composition according to claim 1 consisting essentially of benzocaine, calcium carbonate, xylitol and starch paste.

16. The composition according to claim 1 wherein the amount of sweetener is 30 to 90% by weight of the composition.

17. A sore throat composition consisting essentially of calcium carbonate, benzocaine, a sweetener; 0.5 to 30% by weight of one or more matrix-forming agents, 0.5 to 30% by weight of one or more swellable polymers; and a swelling agent, to thereby provide a sustained release of said antacid, and slow dissolution or disintegration of said composition in the mouth of a subject.

18. The method according to claim 17 wherein the amount of sweetener is 30 to 90% by weight of the composition.

19. A sore throat composition consisting essentially of aluminum hydroxide-magnesium carbonate coprecipitate, magnesium carbonate, calcium carbonate, benzocaine, a sweetener, or combinations thereof; 0.5 to 30% by weight of one or more matrix-forming agents, 0.5 to 30% by weight of one or more swellable polymers; and a swelling agent, to thereby provide a sustained release of said antacid, and slow dissolution or disintegration of said composition in the mouth of a subject.

20. The method according to claim 19 wherein the amount of sweetener is 30 to 90% by weight of the composition.

* * * * *